(12) United States Patent
Jiang (10) Patent No.: US 12,054,712 B2
(45) Date of Patent: Aug. 6, 2024

(54) FRAGMENT SIZE CHARACTERIZATION OF CELL-FREE DNA MUTATIONS FROM CLONAL HEMATOPOIESIS

(71) Applicant: ILLUMINA, INC., San Diego, CA (US)

(72) Inventor: Tingting Jiang, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 439 days.

(21) Appl. No.: 17/022,597

(22) Filed: Sep. 16, 2020

(65) Prior Publication Data

US 2021/0102199 A1    Apr. 8, 2021

Related U.S. Application Data

(60) Provisional application No. 62/912,440, filed on Oct. 8, 2019.

(51) Int. Cl.
| | |
|---|---|
| *C12N 15/11* | (2006.01) |
| *A61K 35/13* | (2015.01) |
| *C07K 16/28* | (2006.01) |
| *C12N 15/10* | (2006.01) |
| *C12Q 1/6869* | (2018.01) |
| *C12Q 1/6886* | (2018.01) |

(52) U.S. Cl.
CPC .............. *C12N 15/11* (2013.01); *A61K 35/13* (2013.01); *C07K 16/2818* (2013.01); *C07K 16/2827* (2013.01); *C12N 15/1003* (2013.01); *C12Q 1/6869* (2013.01); *C12Q 1/6886* (2013.01)

(58) Field of Classification Search
CPC .............. C12Q 1/6869; C12Q 1/6886; C12Q 2600/156; C12Q 2525/204
See application file for complete search history.

(56) References Cited

U.S. PATENT DOCUMENTS

| | | | |
|---|---|---|---|
| 2017/0058332 | A1 | 3/2017 | Kermani et al. |
| 2018/0307796 | A1 | 10/2018 | Jiang et al. |
| 2019/0256924 | A1 | 8/2019 | Vogelstein et al. |
| 2019/0287649 | A1 | 9/2019 | Filippova et al. |

FOREIGN PATENT DOCUMENTS

| | | |
|---|---|---|
| CA | 3122109 | 6/2020 |
| CN | 108603234 | 9/2018 |
| CN | 108885648 | 11/2018 |
| JP | 2018-513508 | 5/2018 |
| JP | 2019-512218 | 5/2019 |

(Continued)

OTHER PUBLICATIONS

Zheng et al. Clincial Chemistry. 2012. 58(3):549-558. (Year: 2012).*

(Continued)

*Primary Examiner* — Joseph G. Dauner
(74) *Attorney, Agent, or Firm* — KNOBBE, MARTENS, OLSON & BEAR LLP (57) ABSTRACT

Methods and systems are provided for differentiating between cancer variants and somatic variants originating from hematopoietic cells in a cell free DNA sample. In some embodiments, the cancer variants can be distinguished from somatic variants originating from hematopoietic cells based on fragment size distribution.

24 Claims, 8 Drawing Sheets

(56) References Cited

FOREIGN PATENT DOCUMENTS

| WO | WO-2016085876 A1 | * | 6/2016 | ........... C12Q 1/6883 |
|----|------------------|---|--------|-------------------------|
| WO | WO 16/149261     |   | 9/2016 |                         |
| WO | WO 2016/149261   |   | 9/2016 |                         |
| WO | WO 17/151524     |   | 9/2017 |                         |
| WO | WO 2017/151524   |   | 9/2017 |                         |
| WO | WO-2018204657 A1 | * | 11/2018 | ........... C12Q 1/6806 |
| WO | WO 2019/169042 A1 |  | 9/2019 |                         |
| WO | WO 2020/132499 A2 |  | 6/2020 |                         |
| WO | WO 2020/186024 A1 |  | 9/2020 |                         |

OTHER PUBLICATIONS

Chan et al. Cancers. 2020. 12:2277. (Year: 2020).*
Wan et al. Nature Reviews Cancer. 2017. 17:223. (Year: 2017).*
Yaung et al. JCO Precis Oncol. 2020. 4:1271-1279. (Year: 2020).*
Abbosh et al. Annals of Oncology. 2019. 30(3):359. (Year: 2019).*
Bauml et al. Clin Cancer Res. 2018. 24(18):4352. (Year: 2018).*
Ptashkin et al. JAMA Oncol. 2018. 4(11):1589-1593. (Year: 2018).*
Hu et al. Clin Cancer Res. 2018. 24(18):4437-4443. (Year: 2018).*
Hastings et al. "Panel-based tumor mutational burden (TMB) analysis of matched tumor and plasma specimens using Illumina's TruSight Oncology 500 next-generation sequencing assay". Q2 Solutions. AACR Annual Meeting, Mar. 29-Apr. 3, 2019. Atlanta, GA. (Year: 2019).*
McLaughlin et al. npj Precision Oncology. 2023. 7:4. (Year: 2023).*
Zink et al. Blood. 2017. 130(6):742-752. (Year: 2017).*
Chan, T. et al., "Development of tumor mutation burden as an immunotherapy biomarker: utility for the oncology clinic", Annals of Oncology, 30, pp. 44-56, Nov. 5, 2018 (May 11, 2018).
Office Action issued in CA application No. 3123297, dated Jun. 23, 2022.
International Search Report and Written Opinion issued in application No. PCT/US2020/050979, dated Nov. 23, 2020.
Office Action issued in JP application No. 2021-537785, dated Jul. 19, 2022.

* cited by examiner

FIG. 7B ically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

FRAGMENT SIZE CHARACTERIZATION OF CELL-FREE DNA MUTATIONS FROM CLONAL HEMATOPOIESIS

CROSS-REFERENCE TO RELATED APPLICATIONS

This application claims priority to U.S. Provisional Application No. 62/912,440, filed on Oct. 8, 2019, which is hereby incorporated by reference in its entirety.

FIELD

Some embodiments of the methods and systems provided herein relate to variant calling from sequence data obtained from a cell free DNA (cfDNA) sample. In some embodiments, a somatic variant originating from a hematopoietic cell can be distinguished from a cancer variant based on fragment size distribution of a plurality of variants.

BACKGROUND

Mutations in the DNA of a person are known to be a cause of cancer and these mutations are now a focus of cancer research and treatment. Circulating tumor DNA (ctDNA) is a noninvasive, real-time biomarker that can provide diagnostic and prognostic information for cancer patients before and after treatment. However, only a small fraction of cell-free DNA (cfDNA) originates from tumor cells, and the majority of fragments come from hematopoietic cells. Somatic mutations harbored by hematopoietic cells can be a major source of false positive mutations in cfDNA affecting clinical decisions.

SUMMARY

The present disclosure relates to methods and systems for distinguishing cancer variants and somatic variants originating from hematopoietic cells from a cfDNA sample.

Some embodiments provided herein relate to methods for differentiating cancer variants from hematopoietic cell variants in a circulating tumor DNA (ctDNA) sample. In some embodiments, the methods include (a) obtaining or having obtained a ctDNA sample comprising a plurality of cell free DNA (cfDNA) fragments; (b) extracting cfDNA fragments from the sample, wherein the cfDNA fragments comprise a plurality of variants; (c) performing molecular profiling for each of the plurality of variants; and (d) identifying cancer variants by removing the identified hematopoietic cell variants. In some embodiments, performing molecular profiling for each of the plurality of variants includes (i) determining a variant allele frequency (VAF) for each of the plurality of variants, wherein the plurality of variants comprise cancer variants and hematopoietic cell variants, and (ii) generating a fragment size distribution profile to identify hematopoietic cell variants.

Some embodiments provided herein relate to methods of determining a tumor mutation burden of a tumor. In some embodiments, the methods include obtaining sequence data from a biological sample comprising a tumor cell; determining a plurality of variants from the sequence data; and determining the number of cancer variants in the plurality of variants using any of the methods described herein, wherein the number of cancer variants is equal to the tumor mutation burden of the tumor.

Some embodiments provided herein relate to methods of treating a tumor. In some embodiments, the methods include determining a tumor having a tumor mutation burden greater than or equal to 10 cancer variants according to any of the methods described herein and treating the tumor by administering an effective amount of a checkpoint inhibitor.

Some embodiments provided herein relate to electronic systems for analyzing genetic variation data. In some embodiments, the systems include an informatics module running on a processor and adapted to identify a plurality of variants from sequence data from a cfDNA sample, wherein the plurality of variants comprises cancer variants and hematopoietic cell variants; an analyzer for performing molecular profiling for each of the plurality of variants, wherein the analyzer is configured to determine a variant allele frequency (VAF) for each of the plurality of variants and configured to generate a fragment size distribution profile; an analyzer for identifying cancer variants by removing identified hematopoietic cell variants; and a display module adapted to return variants not removed from the plurality of variants.

BRIEF DESCRIPTION OF THE DRAWINGS

FIGS. 7A-7B depict tumor mutation burden (TMB).

DETAILED DESCRIPTION

In the following detailed description, reference is made to the accompanying drawings, which form a part hereof. In the drawings, similar symbols typ- Embodiments of the systems, methods, and compositions provided herein relate to methods and systems for determining a nucleic acid variant ("variant calling") from sequence data obtained from a cell free DNA (cfDNA) sample taken from a user or patient. In some embodiments, the methods and systems can distinguish somatic mutations from different cell origins that are unrelated to cancer from tumor mutations based on fragment size distribution. In some embodiments, a somatic variant originating from a hematopoietic cell can be differentiated from a mutation originating from a tumor cell, both obtained from a cfDNA sample, based on the variant's fragment size distribution. A cfDNA sample includes DNA fragments that originate from tumor cells and from other sources, including from clonal hematopoiesis. The fragment size of DNA from tumor cells differs from that of hematopoietic cells, such that fragments from a cfDNA sample can be applied to a fragment size distribution profile for distinguishing between tumor and hematopoietic cells, which can provide improved determination of tumor mutation burden in a sample. More specifically, in some embodiments, fragments carrying somatic mutations from solid tumors have a smaller size relative to fragments carrying somatic mutations from clonal hematopoiesis or from leukemias.

Unless otherwise defined herein, scientific and technical terms used in connection with the present application shall have its ordinary meaning as understood in light of the specification, and as by those of ordinary skill in the art to which this disclosure belongs. It should be understood that this disclosure is not limited to the particular methodology, protocols, and reagents, etc., described herein and as such can vary. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are each incorporated by reference herein in its entirety.

As used herein, "cell-free DNA" or "cfDNA" has its ordinary meaning as understood in light of the specification and refers to freely circulating DNA in the bloodstream, but that may not necessarily be of tumor origin. cfDNA can be released from a cell as a result of various processes, including both normal and abnormal apoptotic events, cellular excretions, necrosis, or the like. Specific forms of cfDNA may be present in the circulatory system as a result of various medical conditions, disease states, or pregnancy. Solid tissues, including cancers, also contribute to the plasma cfDNA pool. cfDNA may be characterized by nucleic acid fragments length due to intranucleosomal fragmentation, wherein the fragments may be a size of about 100 to 200 bp in length, such as 100, 110, 120, 130, 140, 150, 160, 170, 180, 190, or 200 bp in length, or a length within a range defined by any two of the aforementioned values. In some embodiments, the fragment is a length of 166 bp.

As used herein, "circulating tumor DNA" or "ctDNA" has its ordinary meaning as understood in light of the specification and refers to tumor derived fragmented DNA that may not be associated with cells. ctDNA may be from a portion of cfDNA found in blood plasma or serum, and may originate from tumor or from circulating tumor cells. ctDNA bears the molecular signatures of a neoplastic cell genome. Relative to microdissection of tumor tissue, which interrogates a minute and focal fraction of intratumor genetic diversity, ctDNA can be used to sample clonal varieties of both primary and metastatic sites through perfusion sampling. However, ctDNA may be present at low allele frequencies due to dilution by the abundant normal cfDNA. In some embodiments, the low allele frequency is in an amount of less than 5%, less than 4%, less than 3%, less than 2%, less than 1%, less than 0.9%, less than 0.8%, less than 0.7%, less than 0.6%, less than 0.5%, less than 0.4%, less than 0.3%, or less than 0.2%, or in an amount within a range defined by any two of the aforementioned values.

In some embodiments, the methods and systems described herein are capable of differentiating between a somatic variation that originates from a hematopoietic cell and a mutation that originates from a tumor cell.

As used herein, a "variant" can include a polymorphism within a nucleic acid molecule. A polymorphism can include an insertion, deletion, variable length tandem repeats, single nucleotide mutation, and a structural variant such as translocation, copy number variation, or a combination thereof. A variant can include a germline variant or a somatic variant. As used herein, a "germline variant" can include a variant present in germ cells and all cells of an individual, and may be passed on to offspring. As used herein, a "somatic variant" can include a variant present in a tumor cell or harbored by a hematopoietic cell, and not in other cells of an individual, and may not be inherited.

Analysis of genetic mutations can provide valuable information in the study of a variety of phenotypes, including inherited disorders and certain somatic diseases, such as cancer. A variant allele may include a variant form of a gene at a particular position in its DNA sequence. Some genetic sequences vary from one individual to the next with no resultant effect, while others can result in dramatically different phenotypes. For example, a single mutation in a DNA sequence can alter the turning on or off of a gene or the functionality of a protein in a metabolic chain. Genetic data across a population in which genetic variability exists can provide insights not only into the relationship between a gene and a phenotype but also into the evolutionary history of a phenotype associated with a variant. For example changes in biological organs or systems that occur over time, such as kidneys, hair, or musculature changes, can be associated with somatic mutations.

As used herein "variant allele frequency" or "VAF" has its ordinary meaning as understood in light of the specification, and refers to the percentage of sequenced reads observed matching the variant divided by the overall coverage at the target position. VAF may include a measure of the proportion of sequenced reads carrying the variant.

A "hematopoietic cell" has its ordinary meaning as understood in light of the specification, and refers to any type of cell of the hematopoietic system, including, but not limited to, undifferentiated cells such as hematopoietic stem cells and progenitor cells (HSPCs), and differentiated cells such as megakaryocytes, platelets, erythrocytes, leukocytes, granulocytes, monocytes, lymphocytes, and natural killer (NK) cells. As used herein, "clonal hematopoiesis" has its ordinary meaning as understood in light of the specification, and refers to clonal outgrowth of a sub-population of hematopoietic cells having one or more somatic mutations. Clonal hematopoiesis (CH) can be a major source of false positive mutations identified in cfDNA, and may therefore affect clinical decisions. Thus, the present disclosure relates to methods and systems for determining whether somatic mutations originate from CH or tumor cells.

Clonal hematopoiesis of indeterminate potential (CHIP) may be a common aging-related phenomenon in which hematopoietic stem cells (HSCs) or other early blood cell progenitors contribute to the formation of genetically distinct subpopulation of blood cells. In some embodiments, determination of somatic variant origination can indicate the tumor mutation burden (TMB) of a tumor. In some embodiments, determination of somatic variant origination can be used for determination of target therapy.

As used herein "tumor mutation burden" or "TMB" has its ordinary meaning as understood in light of the specification, and refers to a measurement of mutations carried by tumor cells. TMB has emerged as an important biomarker for cancer therapy selection after recent studies have shown a correlation between TMB and the effectiveness of checkpoint inhibitor immunotherapies. In calculating the TMB, it may be useful to identify and filter out germline variants. The germline variants may include variants that an individual is born with (or shared between the tumor and the normal cell) but which are detected as variants in comparison to the reference genome. These variants do not contribute to distinguishing tumor cells from normal cells, and thus can lead to over estimation of the TMB if not correctly filtered out. Furthermore, somatic variants originating from hematopoietic cells (for example, clonal hematopoiesis) can also be filtered out to distinguish tumor cells from clonal hematopoiesis. Embodiments include determining a TMB for a cfDNA sample, selecting a treatment for the tumor according to the TMB, and administering the treatment to a subject in need thereof.

In some embodiments, TMB may be calculated by determining the eligible variants divided by the effective panel size. Eligible variants include, for example, variants in the coding region, variants that do not appear in low confidence regions, variants having frequencies of more than 0.4% and less than 40%, variants having a coverage of more than 500 times, single nucleotide variants (excluding multiple nucleotide variants) insertion and deletion variants (Indels), non-synonymous and synonymous variants, excluding variants with a COSMIC (catalogue of somatic mutations in cancer) count of greater than 50, and/or excluding variants with mutations in a clonal hematopoiesis affected gene, such as Tet methylcytosine dioxygenase 2 (TET2), tumor protein p53 (TP53), DNA (cytosine-5)-methyltransferase 3A (DNMT3A), and/or casitas B-lineage lymphoma (CBL). Effective panel size can include, for example, the total coding region with a coverage of greater than 500 times. Methods Some embodiments provided herein relate to a method for determining somatic variant origination. In some embodiments, the method includes differentiating DNA mutations derived from clonal hematopoiesis (CH) from DNA mutations that indicate a tumor variant in a cfDNA sample. In some embodiments, CH can be differentiated from tumor variants by analyzing the fragment size distribution of DNA fragments in the cfDNA.

As used herein, "fragment size distribution" has its ordinary meaning in light of the specification, and refers to distributing fragments of cfDNA by size to generate a fragment size profile. The generated fragment size profile can be used to differentiate somatic mutations from different cell origins.

Figure 1:
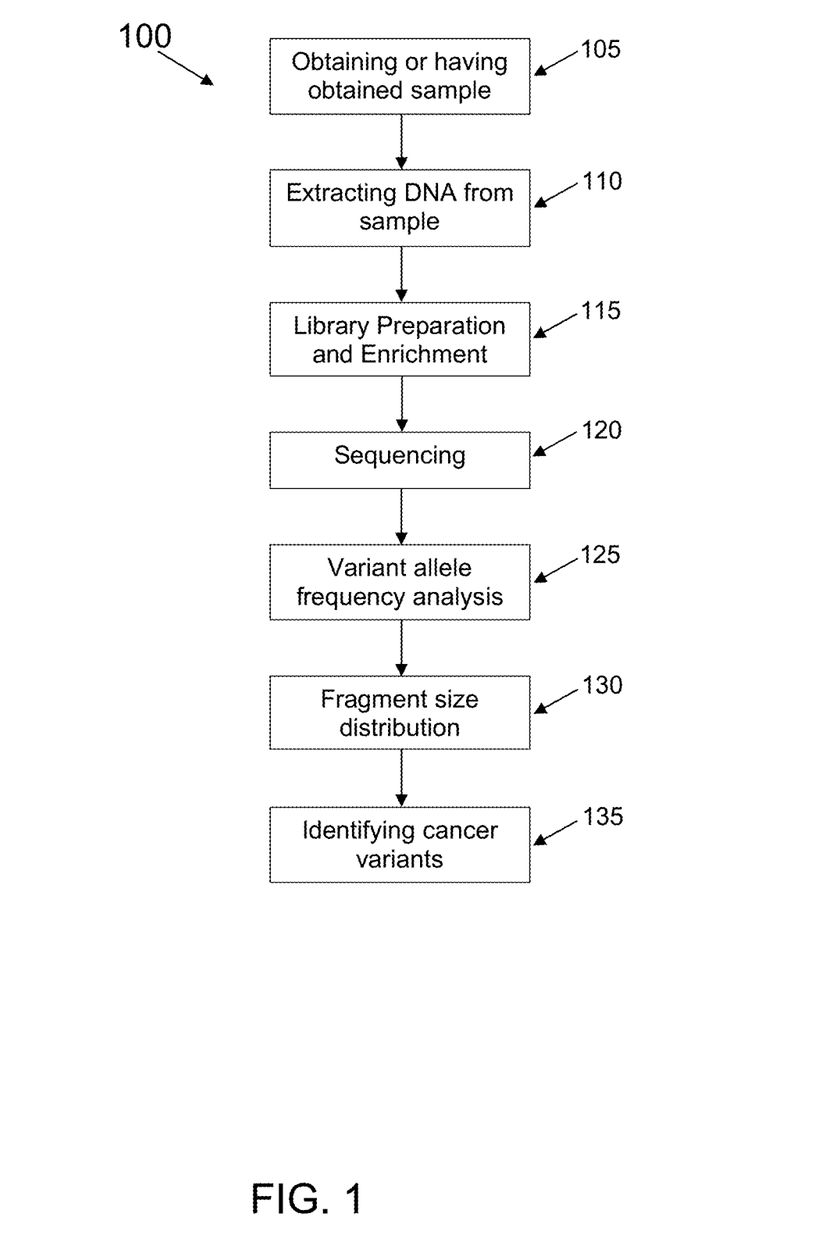
FIG. 1 illustrates a flow diagram of an example method for differentiating between cancer variants and somatic variants originating from hematopoietic cells.

An exemplary method for differentiating somatic mutations from different cell origins is set forth schematically in FIG. 1. The method 100 includes step 105 of obtaining or having obtained a sample. In some embodiments, the sample is a biological sample. In some embodiments, a biological sample can include a tumor cell. In some embodiments, a biological sample can include a serum sample, a stool sample, a blood sample, and a tumor sample. In some embodiments, the biological sample is fixed. In some embodiments, the sample includes cfDNA. In some embodiments, the sample includes ctDNA. In some embodiments, the sample includes a plurality of variants, including, for example, somatic and germline variants. In some embodiments, the methods include removing a germline variant.

An amount of biological sample is not specifically required, so long as the biological sample contains sufficient nucleic acids for analysis. Thus, an amount of biological sample may include from about 1 µL to about 500 µL, such as 1, 2, 3, 4, 5, 6, 7, 8, 9, 10, 15, 20, 25, 30, 35, 40, 45, 50, 60, 70, 80 90, 100, 150, 200, 250, 300, 350, 400, 450, or 500 µL, or an amount within a range defined by any two of the aforementioned values.

In some embodiments, the method includes obtaining a sample from the subject. In some embodiments, the methods includes having a sample obtained from a subject. In some embodiments, a subject can provide a biological sample, or a separate entity can provide a biological sample. The biological sample can be any substance that is produced by the subject. Generally, the biological sample may be any tissue taken from the subject or any substance produced by the subject. Examples of biological samples can include blood, plasma, saliva, cerebrospinal fluid (CSF), cheek tissue, urine, feces, skin, hair, organ tissue. In some embodiments, the biological sample is a solid tumor or a biopsy of a solid tumor. In some embodiments, the biological sample is a formalin-fixed, paraffin-embedded (FFPE) tissue sample. The biological sample can be any biological sample that comprises nucleic acids. Biological samples may be derived from a subject. The subject may be a mammal, a reptile, an amphibian, an avian, or a fish. In some embodiments, the subject is a human. In some embodiments, the method further includes obtaining matched tumor samples. By matching tumor and cfDNA variant results, a fragment size profile can be constructed that originates from tumor, healthy, and abnormal hematopoietic cells.

In some embodiments, the method 100 includes step 110 of extracting DNA from the sample. The DNA of the biological sample may be extracted by any suitable extraction method. Methods of achieving this would be well known to the person of skill in the art and include, for example, phenol/chloroform extraction, ethanol precipitation, cesium chloride gradients, CHELEX or silica column, or bead methods. DNA may be extracted from cells using methods known in the art and/or commercially available kits, e.g., by using the QIAamp DNA blood Mini Kit or the DNeasy Blood & Tissue Kit supplied by QIAGEN.

In some embodiments, the method 100 includes step 115 of library preparing and enrichment. Library preparation and enrichment can be performed according to methods known in the art. For example, the method of library preparation and enrichment may include standard protocols including the steps of end repair and A-tailing, adapter ligation, ligation clean up, index PCR, first hybridization, first target capture, second hybridization, second target capture, amplification of library, clean up amplified library, library quantification, and/or library normalization.

In some embodiments, the method 100 further includes step 120 of sequencing. Sequencing of the DNA libraries can be performed, for example, using HiSeq. HiSeq may be performed with 151 bp paired end reads. Paired-end sequencing provides high-quality alignment across DNA regions containing repetitive sequences, and produces long contigs for de novo sequencing by filling gaps in the consensus sequence. Paired-end DNA sequencing also detects common DNA rearrangements such as insertions, deletions, and inversions. In some embodiments, sequencing includes molecular profiling using unique molecular identifiers (UMI).

In some embodiments, the method 100 further includes step 125 of variant allele frequency (VAF) analysis. VAF analysis may be performed according to methods established in the art, wherein the proportion of reads at a site which contains a variant allele is determined. In cfDNA, VAF may be significantly different between germline and somatic lines due to low tumor fractions, typically at an amount of less than 20%. ctDNA may include highly sensitive detection of low VAF variants in an amount of 0.2% to 0.4%.

Variant frequency analysis may include removing variant data from the sequence data gathered from a sequencer. A germline variant can be removed, for example, by applying a filter to data representing a plurality of variants, such as a database filter or a proximity filter. The database filter can be used to identify a variant as a germline variant, and remove the variant from the data representing the plurality of variants in the sample. The database filter can be related to an allele count of a corresponding variant in a database, for a particular variant of the plurality of variants. The proximity filter can be related to the allele frequency of a certain variant of the plurality of variants, the location of the variant in region of a genome, and the proximity of the allele frequency of the variant to the allele frequency of identified germline variants in the same region of a genome. In some embodiments, applying a database filter includes determining first germline variants in the plurality of variants, wherein the first germline variants each have an allele count in a first reference set of variants greater than or equal to a threshold allele count. In some embodiments, applying a proximity filter includes: (i) binning variants of the plurality of variants into a plurality of bins, wherein variants located in the same region of a genome are binned into the same bin; (ii) determining database variants in the plurality of variants, wherein a database variant is present in a second reference set of variants; and/or (iii) determining second germline variants in the plurality of variants, wherein the second germline variants each have an allele frequency within a proximate range of an allele frequency of at least one database variant in the same bin as the second germline variant.

In some embodiments, variants of the plurality of variants can be sorted or binned into a plurality of bins, such that variants located in the same region of a genome are sorted or binned into the same bin. In some embodiments, the same region of a genome can be within the same chromosome, within the same arm of a chromosome, within the same chromosomal cytoband. In some embodiments, the same region of a genome can be within the same contiguous 100 Mb, 50 Mb, 40 Mb, 30 Mb, 20 Mb, 10 Mb, 5 Mb, 1 Mb, or within any range between any two of the foregoing numbers.

In some embodiments, the proximity filter also includes instructions or commands for determining which binned variants are readily identifiable as germline variants. For example, a binned variant can have a corresponding variant present in one or more reference databases and be identified as a germline variant.

In some embodiments, the proximity filter includes instructions for determining that variants having an allele frequency greater than or equal to a threshold frequency in the sample are germline variants. In some such embodiments, variants having an allele frequency greater than or equal to 0.7, 0.8, 0.9, or 1.0 can be identified as germline variants, although it should be realized that higher or lower allele frequencies are still within the scope of the present disclosure.

In some embodiments, the proximity filter includes instructions for determining a proximate range of an allele frequency for a variant that has not been identified as a germline variant. A proximate range of an allele frequency for a variant can include a range of allele frequencies above and below the allele frequency of the variant. In some embodiments, the proximate range is a range having a maximum and a minimum from the allele frequency of variant of 0.01, 0.02, 0.03, 0.04, 0.05, 0.06, 0.07, 0.08, 0.09, or any number within a range between any two of the foregoing numbers. For example, for a variant having an allele frequency of 0.2 and a proximate range of 0.05, the minimum and maximum of the proximate range would be allele frequencies of 0.15 and 0.25, respectively.

In some embodiments, the proximate range is determined by the value of two (n) standard deviations of a binomial distribution assuming the supporting evidence for the given variant is generated by a binomial process. For example, for a variant having an allele frequency (x), with a coverage (y), the proximate range (z) can be:

$$z = n*\mathrm{sqrt}(y*x*(1-x))/y$$

For example, for a variant having an allele frequency of 0.2, a coverage/depth of sequencing of 100, the proximate range would be 0.08, and the minimum and maximum of the proximate range would be allele frequencies of 0.12 and 0.28, respectively. In some embodiments, the proximate range is the higher of either 0.05, or two (n) standard deviations from a binomial distribution of the allele frequency of the variant, above and below the allele frequency of the variant.

In some embodiments, a variant can be identified as a germline variant if the variant has an allele frequency within proximate range of one or more identified germline variants in the same bin as the variant. In some embodiments, a variant can be identified as a germline variant if the variant has an allele frequency within proximate range of more than 1, 2, 3, 4, 5, 6, 7, 8, 9, or 10 identified germline variants in the same bin as the variant. In some embodiments, a variant can be identified as a germline variant if the variant has an allele frequency within proximate range of more than 5 identified germline variants in the same bin as the variant. For example, in an embodiment in which a variant would be identified as a germline variant if the variant has an allele frequency within proximate range of more than 5 identified germline variants in the same bin as the variant: a variant having an allele frequency of 0.2, with a proximate range of 0.05, thus having a minimum range of 0.15 and a maximum range of 0.25 and binned in a bin representing chromosome 7 would be identified as a germline variant where more than 5 identified germline variants having allele frequencies in proximate range of the variant and binned in the bin representing chromosome 7.

In some embodiments, the proximity filter identifies somatic variants which are variants not identified as germline variants. In some embodiments, the number of somatic variants obtained from sequencing data from a tumor is the tumor mutation burden of the tumor.

In some embodiments, the database filter or the proximity filter can be applied to the plurality of variants to identify and remove germline variants from the plurality of variants. In some embodiments, the database filter and the proximity filter can be applied consecutively. For example, the output of the database filter such can be used for the input of the proximity filter. Conversely, the output of the proximity filter can be used as the input of the database filter.

In some embodiments, after performing the variant allele frequency analysis at step 125, the method 100 further includes step 130 of fragment size distribution. Fragment size may be inferred using consensus sequences after read collapsing using genomic coordinates. In some embodiments, fragment size distribution includes generating a profile of fragment size based on variant types of different cell origin, such that different cell origin or different variant types generate distinct fragment size profiles. In some embodiments, the fragment size provide is dependent on cell lineage.

In some embodiments, the method 100 includes step 135 of identifying cancer variants. Identifying cancer variants can be performed by analyzing the fragment size distribution and removing the fragment size distribution that is known to be associated with CH. In some embodiments, identifying cancer variants includes fitting the fragment size distribution to a likelihood model. In some embodiments, matched tumor samples are analyzed using method 100 set forth in FIG. 1, wherein matching tumor and cfDNA variant results, enables construction of a fragment size profile that originates from tumor, healthy, and abnormal hematopoietic cells. To identify somatic mutations from CH, a likelihood ratio test of fitting observed fragment sizes of different cell origins may be performed. In some embodiments, identifying cancer variants is performed at a sensitivity of greater than 75%, such as greater than 75, 80, 85, 90, 95, 96, 97, 98, or 99%, or at a sensitivity within a range defined by any two of the aforementioned values.

Methods of Treatment

Some embodiments of the methods and systems include methods of treating a subject having or suspected of having a tumor. In some such embodiments, the number of cancer variants present in cfDNA sample can be determined by the methods and systems provided herein. For example, sequence data can be obtained from a cfDNA sample, a plurality of variants can be identified from the sequence data, and a fragment size distribution profile can be established to identify and delineate CH from cancer variants, thereby identifying cancer variants in the plurality of variants. In some embodiments, the number of cancer variants obtained from sequencing data from a cfDNA sample is the TMB. In some embodiments, TMB is calculated as an average number of cancer variants per genomic region, such as, for example, mutations per 50 kb, 100 kb, 1 Mb, 10 Mb, 100 Mb, and the like. TMB can be sampled by sequencing an entire genome or a portion thereof. For example, a portion of a genome may be sequenced by enriching for one or more genomic regions of interest, such as a tumor gene panel, a full exome, a partial exome, and the like.

Some embodiments of treating a subject having or suspected of having a tumor can include determining that a cfDNA sample has a TMB greater than or equal to a TMB threshold, and contacting the tumor with an effective amount of therapeutic agent. Some embodiments include treating a subject having a tumor and can include determining that a cfDNA sample has a TMB greater than or equal to a TMB threshold, and administering to the subject an effective amount of therapeutic agent. In some embodiments, a TMB threshold can be 2, 3, 4, 5, 6, 7, 8, 9, 10, 15, 20, 30, 40, 50, 60, 70, 80, 90, 100, 200, 300, 400, 500, 600, 700, 800, 900, 1000 or any number in a range between any two of the foregoing numbers.

In some embodiments, TMB is calculated by determining the eligible variants divided by the effective panel size. Eligible variants include, for example, variants in the coding region, variants not in low confidence regions, variants have a frequencies of more than 0.4% and less than 40%, variants having a coverage of more than 500 times, single nucleotide variants (excluding multiple nucleotide variants) and insertion and deletion variants (Indels), nonsynonymous and synonymous variants, excluding variants with a COSMIC count of greater than 50, and/or excluding variants with mutations in TET2, TP53, DNMT3A, and/or CBL. Effective panel size can include, for example, the total coding region with a coverage of greater than 500 times.

Examples of therapeutic agents include chemotherapeutic agents. In some embodiments, the therapeutic agent can include a checkpoint inhibitor. Examples of checkpoint inhibitors include a CTLA-4 inhibitor, a PD-1 inhibitor, and a PD-L1 inhibitor. In some embodiments, the checkpoint inhibitor can include Ipilimumab, Nivolumab, Pembrolizumab, Spartalizumab, Atezolizumab, Avelumab, and Durvalumab. Examples of tumors include a colorectal tumor, a lung tumor, an endometrium tumor, a uterine tumor, a gastric tumor, a melanoma, a breast tumor, a pancreatic tumor, a kidney tumor, a bladder tumor, and a brain tumor. More examples of cancers that can be treated with the methods and systems included herein are listed in U.S. 2018/0218789, which is expressly incorporated by reference herein in its entirety.

Systems

Some embodiments include computer-based systems and computer implemented methods for performing the methods described herein. In some embodiments, the systems can be used for determining a fragment size distribution profile for differentiating between CH and cancer variants. In some embodiments, the systems further include a database filter and/or a proximity filter to be applied to the variation data to identify and remove germline variants. Some embodiments of the methods and systems provided herein include an electronic system for analyzing variation data. In some such embodiments, the systems and computer-implemented methods include an analyzer for variant allele frequency and for fragment size distribution. Some embodiments can include an informatics module running on a processor and adapted to identify a plurality of variants from sequence data from a biological sample, in which the plurality of variants comprises CH and cancer variants. Some embodiments provided herein include computer-implemented methods for identifying CH in a plurality of variants. Some such embodiments can include receiving a plurality of variants from sequence data from a biological sample, the plurality of variants can include CH and cancer variants. Some embodiments include matching tumor and cfDNA variant results to construct a fragment size profile that originates from tumor, healthy, and abnormal hematopoietic cells. In some embodiments, the tumor variants obtained from sequencing data from a cfDNA sample is the TMB.

The system can comprise one or more client components. The one or more client components can comprise a user interface. The system can comprise one or more server components. The server components can comprise one or more memory locations. The one or more memory locations can be configured to receive a data input. The data input can comprise sequencing data. The sequencing data can be generated from a nucleic acid sample from a subject. The system can further comprise one or more computer processor. The one or more computer processor can be operably coupled to the one or more memory locations. The one or more computer processor can be programmed to map the sequencing data to a reference sequence. The one or more computer processor can be further programmed to determine a presence or absence of a plurality of variants from the sequencing data. The one or more computer processor can be further programmed to determine variant allele frequencies. The one or more computer processor can be further programmed to determine a fragment size distribution profile. The one or more computer processor can be further programmed to determine a classification of mutations of different origins by fragment size distribution. The one or more computer processor can be further programmed to generate an output for display on a screen. The output can comprise one or more reports identifying the CH and/or the cancer variant.

Some embodiments of the methods and systems can comprise one or more client components. The one or more client components can comprise one or more software components, one or more hardware components, or a combination thereof. The one or more client components can access one or more services through one or more server components. The one or more services can be accessed by the one or more client components through a network. "Services" is used herein to refer to any product, method, function, or use of the system. For example, a user can place an order for a genetic test. The order can be placed through the one or more client components of the system and the request can be transmitted through a network to the one or more server components of the system. The network can be the Internet, an internet and/or extranet, or an intranet and/or extranet that is in communication with the Internet. The network in some cases is a telecommunication and/or data network. The network can include one or more computer servers, which can enable distributed computing, such as cloud computing. The network, in some cases with the aid of the computer system, can implement a peer-to-peer network, which may enable devices coupled to the computer system to behave as a client or a server.

Some embodiments of the systems can comprise one or more memory locations, such as random-access memory, read-only memory, flash memory; electronic storage unit, such as hard disk; communication interface, such as network adapter, for communicating with one or more other systems; and/or peripheral devices, such as cache, other memory, data storage and/or electronic display adapters. The memory, storage unit, interface, and/or peripheral devices may be in communication with the CPU through a communication bus, such as a motherboard. The storage unit can be a data storage unit or data repository for storing data. In one example, the one or more memory locations can store the received sequencing data.

Some embodiments of the methods and systems can comprise one or more computer processors. The one or more computer processors may be operably coupled to the one or more memory locations to e.g., access the stored sequencing data. The one or more computer processors can implement machine executable code to carry out the methods described herein. For instance, the one or more computer processors can execute machine readable code to map a sequencing data input to a reference sequence, and/or identify CH and/or cancer variants.

Some embodiments of the methods and systems provided herein can include machine executable or machine readable code. In some such embodiments, the machine executable or machine readable code can be provided in the form of software. During use, the code can be executed by the processor. In some cases, the code can be retrieved from the storage unit and stored on the memory for ready access by the processor. In some embodiments, the electronic storage unit can be precluded, and machine-executable instructions are stored on memory. The code can be pre-compiled and configured for use with a machine having a processer adapted to execute the code, can be compiled during runtime, or can be interpreted during runtime. The code can be supplied in a programming language that can be selected to enable the code to execute in a pre-compiled, as-compiled or interpreted fashion.

Some embodiments of the systems and methods provided herein, such as the computer system, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Some embodiments of the methods and systems disclosed herein can include or be in communication with one or more electronic displays. The electronic display can be part of the computer system, or coupled to the computer system directly or through the network. The computer system can include a user interface (UI) for providing various features and functionalities disclosed herein. Examples of UIs include, without limitation, graphical user interfaces (GUIs) and web-based user interfaces. The UI can provide an interactive tool by which a user can utilize the methods and systems described herein. By way of example, a UI as envisioned herein can be a web-based tool by which a healthcare practitioner can order a genetic test, customize a list of genetic variants to be tested, and receive and view a biomedical report.

Some embodiments of the methods and systems disclosed herein may comprise biomedical databases, genomic databases, biomedical reports, disease reports, case-control analysis, and rare variant discovery analysis based on data and/or information from one or more databases, one or more assays, one or more data or results, one or more outputs based on or derived from one or more assays, one or more outputs based on or derived from one or more data or results, or a combination thereof.

EXAMPLES

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims. The disclosure of each reference set forth herein is incorporated herein by reference in its entirety, and for the disclosure referenced herein.

Example 1

Variant Allele Frequency Determination for FFPE Vs Plasma Samples

Sequence data was obtained from cell-free DNA (cfDNA) and matched tumor samples. The samples were collected across four original tissue types by different tumor stages, including solid tumor and leukemia. In total, 85 plasma samples across four tissue types were analyzed, with 15 bladder and 32 lung samples matched with FFPE tissue, as shown in Table 1

TABLE 1

| Type | Plasma Samples | Tissue Samples |
| --- | --- | --- |
| Leukemia | 5 | N/A |
| Bladder | 15 | 15 |
| Lung | 55 | 32 |
| Healthy | 10 | N/A |

Figure 2:
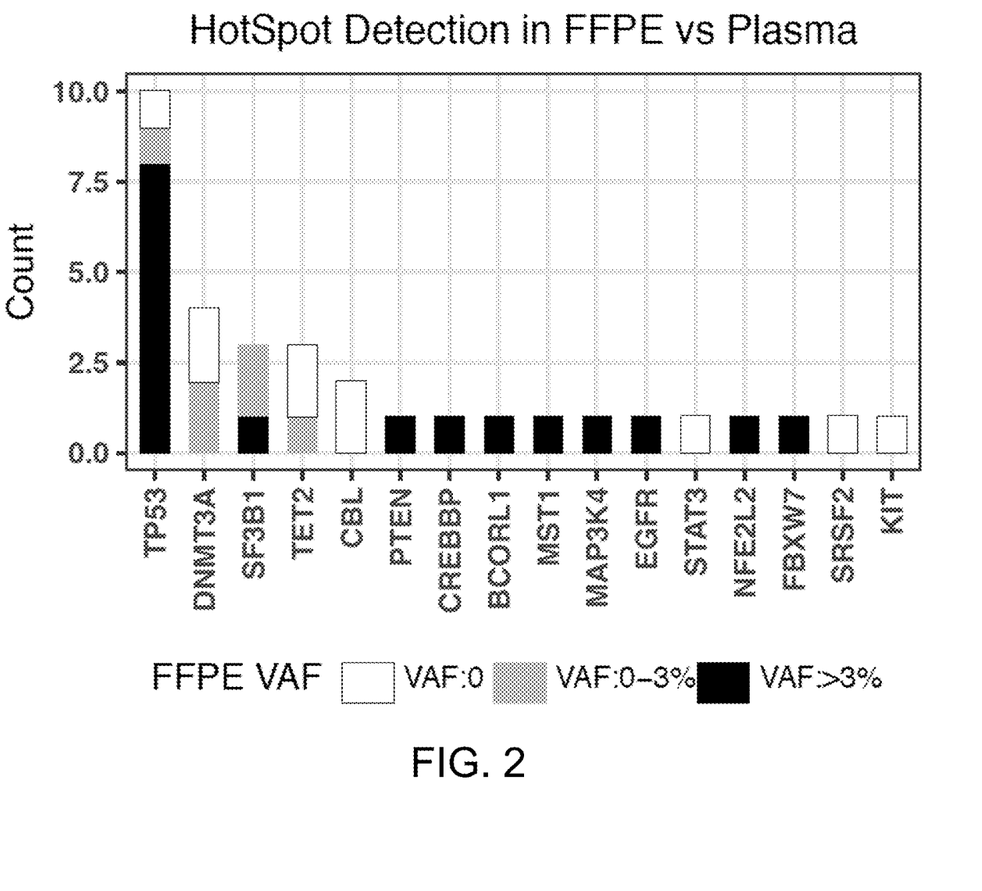
FIG. 2 depicts exemplary results of variant concordance between solid FFPE tissue samples and plasma samples.

FIG. 2 depicts the variant allele frequency determination between FFPE and plasma samples. As shown in FIG. 2, among the 47 samples with matched FFPE and plasma, 33 COSMIC hotspot variants were detected in plasma. Of the 33 variants, 17 variants were detected in FFPE with a VAF of >3%, six with a VAF of ≤3%, and ten wild type FFPE. As shown, most mutations that were found only within the plasma samples but not the FFPE samples were clustered in TP53, DNMT3A, TET2, SF3B1, and CBL, which are known to be associated with clonal hematopoiesis (CH). CH mutations were also detected in FFPE samples with low variant allele frequency.

Figure 3:
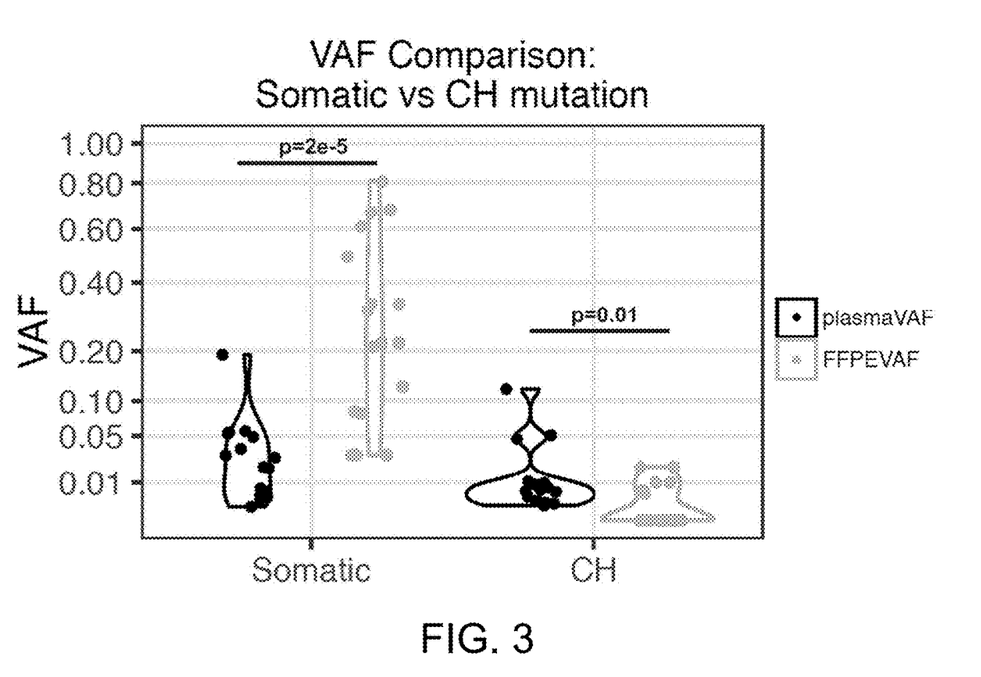
FIG. 3 depicts exemplary results of variant allele frequency comparison between somatic and clonal hematopoiesis mutations between solid tissue and plasma samples.

FIG. 3 depicts a comparison of VAF between somatic and CH mutations. As shown in FIG. 3, the VAF of somatic mutations is significantly higher in FFPE ($p=2e^{-5}$), which is likely due to tumor shedding, whereas the VAF of CH mutations is significantly higher in plasma samples ($p=0.01$).

Example 2

Fragment Size Distribution

The determination of VAF as shown in Example 1 was used to construct a fragment size profile. The fragment size profile originated from the tumor, healthy, and abnormal hematopoietic cells. Three major variant types are present in the plasma, somatic, CH, and germline. These originate from different tissue origins, as shown in Table 2.

TABLE 2

| Variant Type | Sample Type | Cell Origin |
| --- | --- | --- |
| Clonal Hematopoiesis | N/A | Hematopoietic stem cell |
| Germline | Leukemia/Healthy | Blood cell |
| | Solid tumor | Blood or epithelial cell |
| Somatic | Leukemia | Abnormal blood cell |
| | Solid tumor | Malignant epithelial cell |

Figure 4:
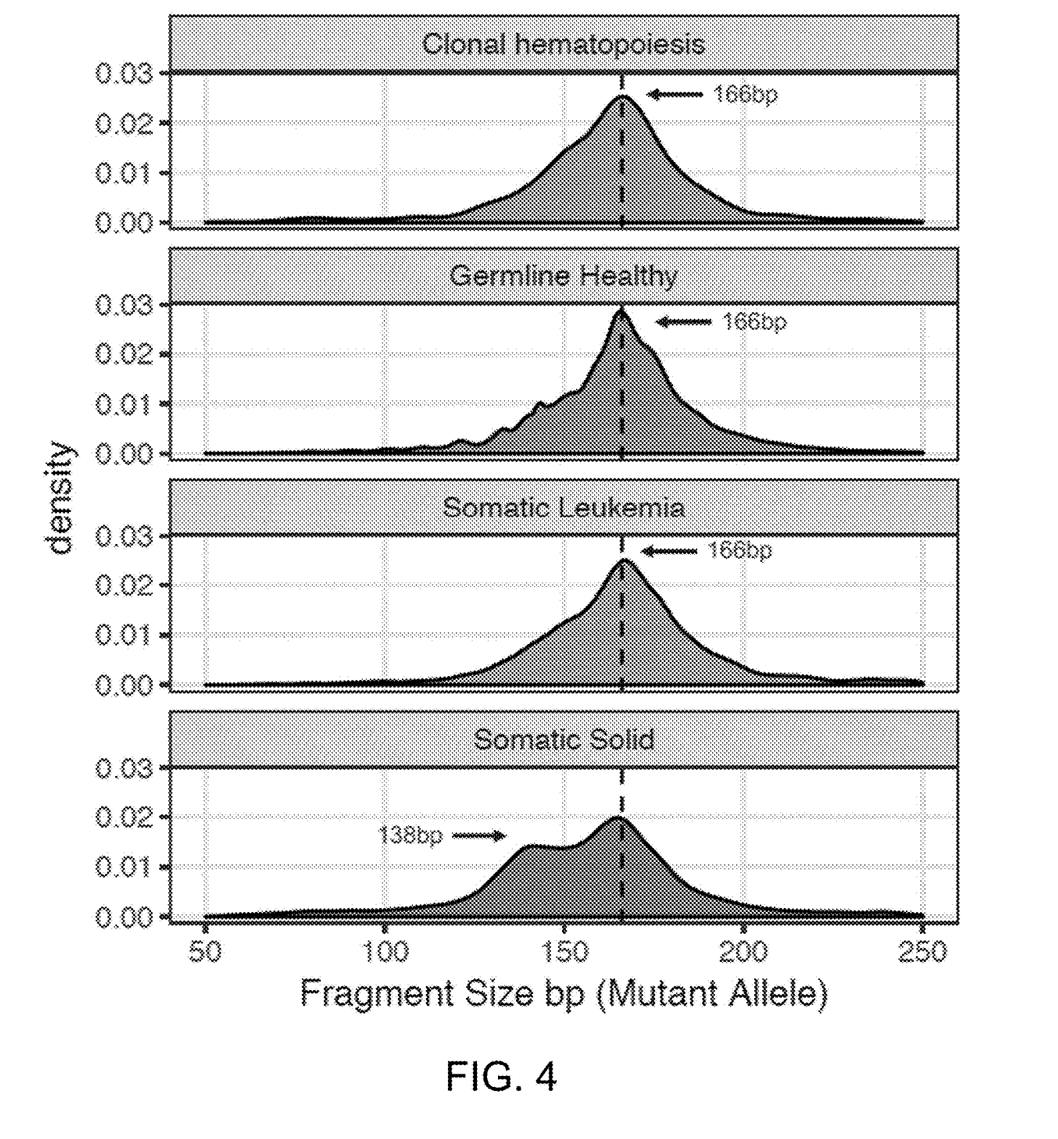
FIG. 4 depicts fragment size distribution of mutations from samples originating from clonal hematopoiesis, germline healthy samples, somatic leukemia, or somatic solid samples.

The fragment size difference between variant types and different tissue origins were determined by extracting the fragments from the sequencing data that carried the mutant allele. The results were aggregated across all samples. As shown in FIG. 4, the fragment size distribution of mutations was found to differ from different origins. The size distribution of fragments carrying somatic mutations from solid tumors (peak at 138 bp) shifted relative to fragments carrying somatic mutations from CH or leukemias (peak at 166 bp). No significant difference in size distribution was seen between fragments carrying somatic mutations and healthy hematopoietic cells (p-value=0.86).

Figure 5:
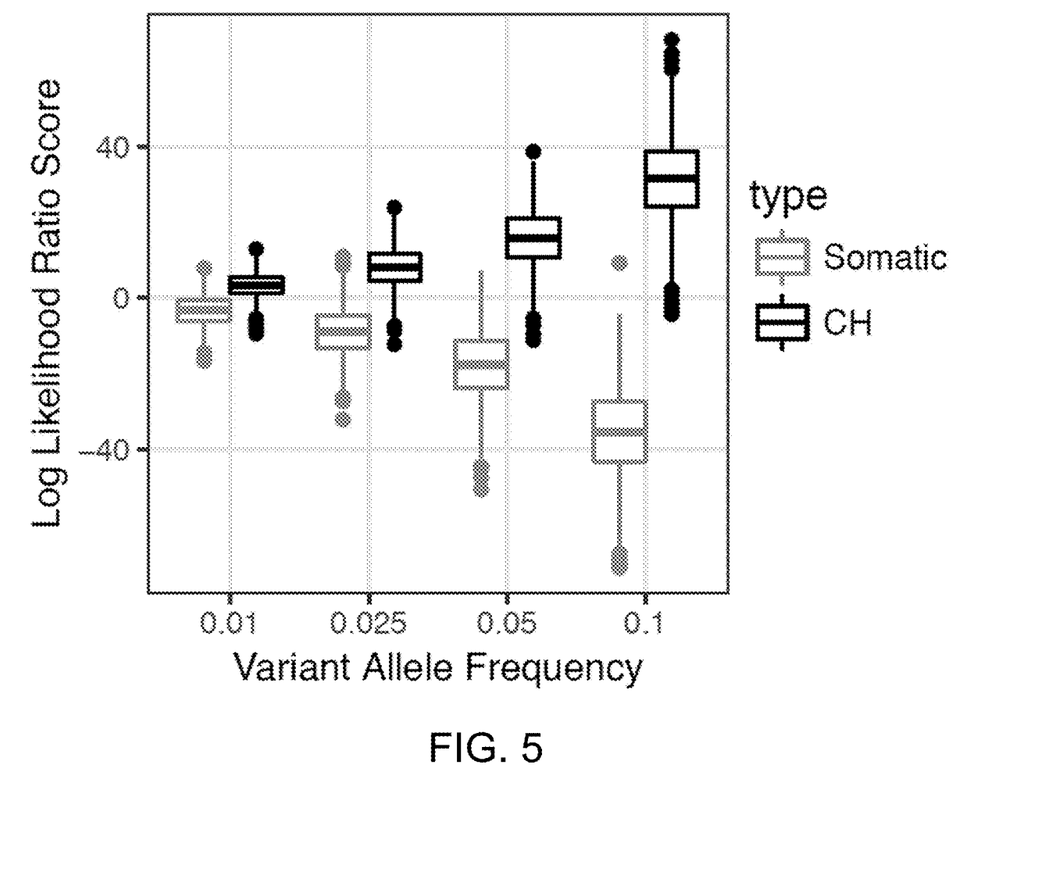
FIG. 5 depicts classification of mutations in somatic or clonal hematopoiesis (CH) cells of different origins by fragment size distribution.

As shown in FIG. 5, the mutations of different origins were classified by fragment size distribution. 10,000 CH or somatic mutations of different VAF were simulated in silico with 2000× coverage by mixing fragments of different origins. By fitting the fragment size distribution by a likelihood model, sensitivities of 81.5%, 92.5%, 98.3%, and 99.8% were achieved, with specificities of 82%, 92.5%, 97.5%, and 99.9%, for 1%, 2.5%, 5%, and 10% CH mutations, respectively.

These examples demonstrate that fragment size distribution of cfDNA released by malignant or healthy hematopoietic cells is different from that of cfDNA released by solid tumors. In addition, the fragment size distribution can be used to differentiated between somatic mutations of different cell origins.

Example 3

Clonal Hematopoiesis Variants in cfDNA

Figure 6:
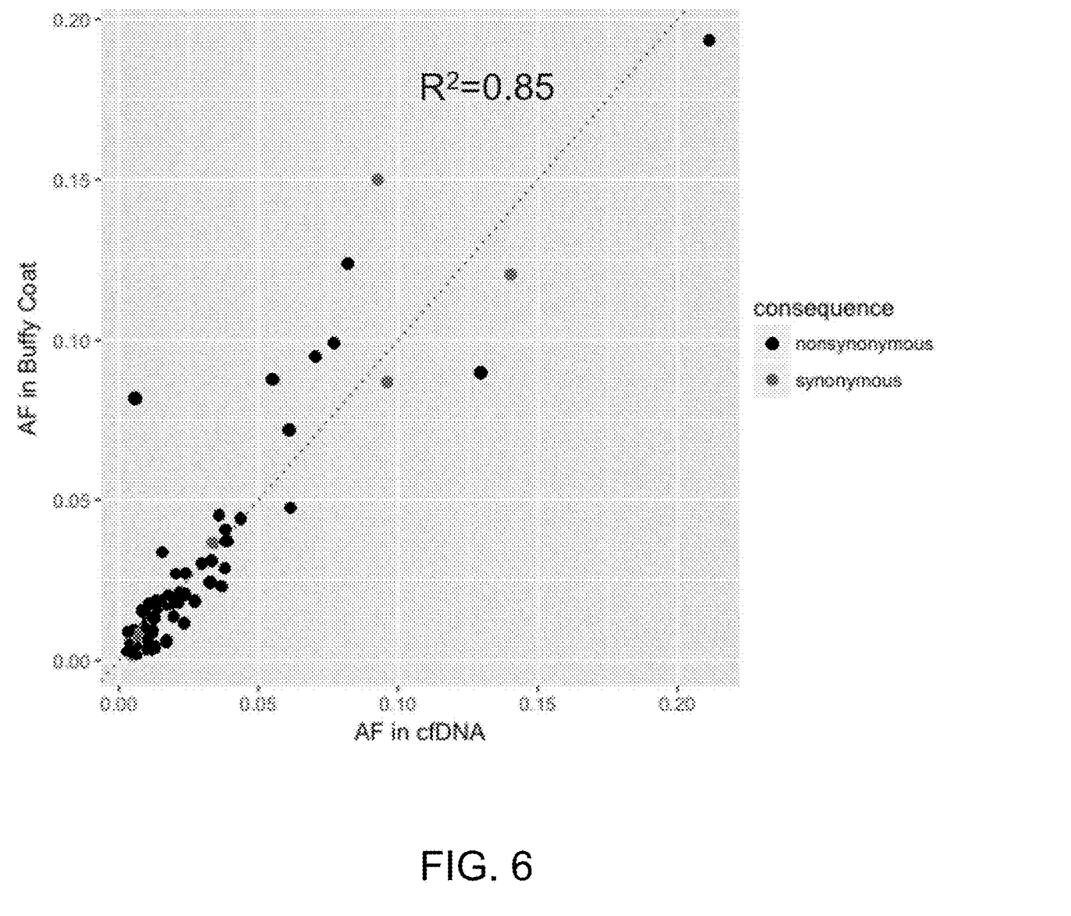
FIG. 6 depicts a correlation of variant allele frequencies of clonal hematopoiesis variants in cfDNA with variant allele frequencies of variants observed in white blood cells (buffy coat).

Forty pairs of cfDNA and buffy coat (white blood cells) DNA were profiled using the method set forth in FIG. 1. Variants were observed in both cfDNA and in buffy coat as non-germline (having a low VAF). The results included 106 variants, of which 92 were nonsynonymous, and 14 were synonymous. As shown in FIG. 6, the VAF determined for cfDNA correlates with the VAF determined for buffy coat.

Example 4

Measuring Tumor Mutational Burden

Tumor mutational burden was determined using the samples analyzed for Example 3. The samples included 40 pairs of cfDNA and buffy coat DNA, which was profiled using the method set forth in FIG. 1.

Raw TMB was calculated by determining the eligible variants divided by the effective panel size. Eligible variants included variants in the coding region, variants not in low confidence regions, variants have a frequencies of more than 0.4% and less than 40%, variants having a coverage of more than 500×, single nucleotide variants (SNVs) and insertion and deletion variants (Indels), nonsynonymous and synonymous variants, excluding variants with a COSMIC count of greater than 50, excluding multiple nucleotide variants (MNVs), and excluding variants with mutations in TET2, TP53, DNMT3A, and/or CBL. The effective panel size included the total coding region with a coverage of greater than 500×. In this example, the total variants included 1025, variants post germline filtering included 121, variants in eligible region included 86, SNVs and Indels in eligible region included 81, variant count after COSMIC removal included 80, variant count about 0.4% included 78, and variant count excluding genes TET2, TP53, DNMT3A, and CBL included 75 variants. Thus, the eligible variants totaled 76. The effective panel size was 1.307291 Mb. The raw TMB was 76/1.30729=57.4 mutations/Mb. The adjusted TMB was (57.37055−1.5)/0.91=61.4.

Figure 7A:
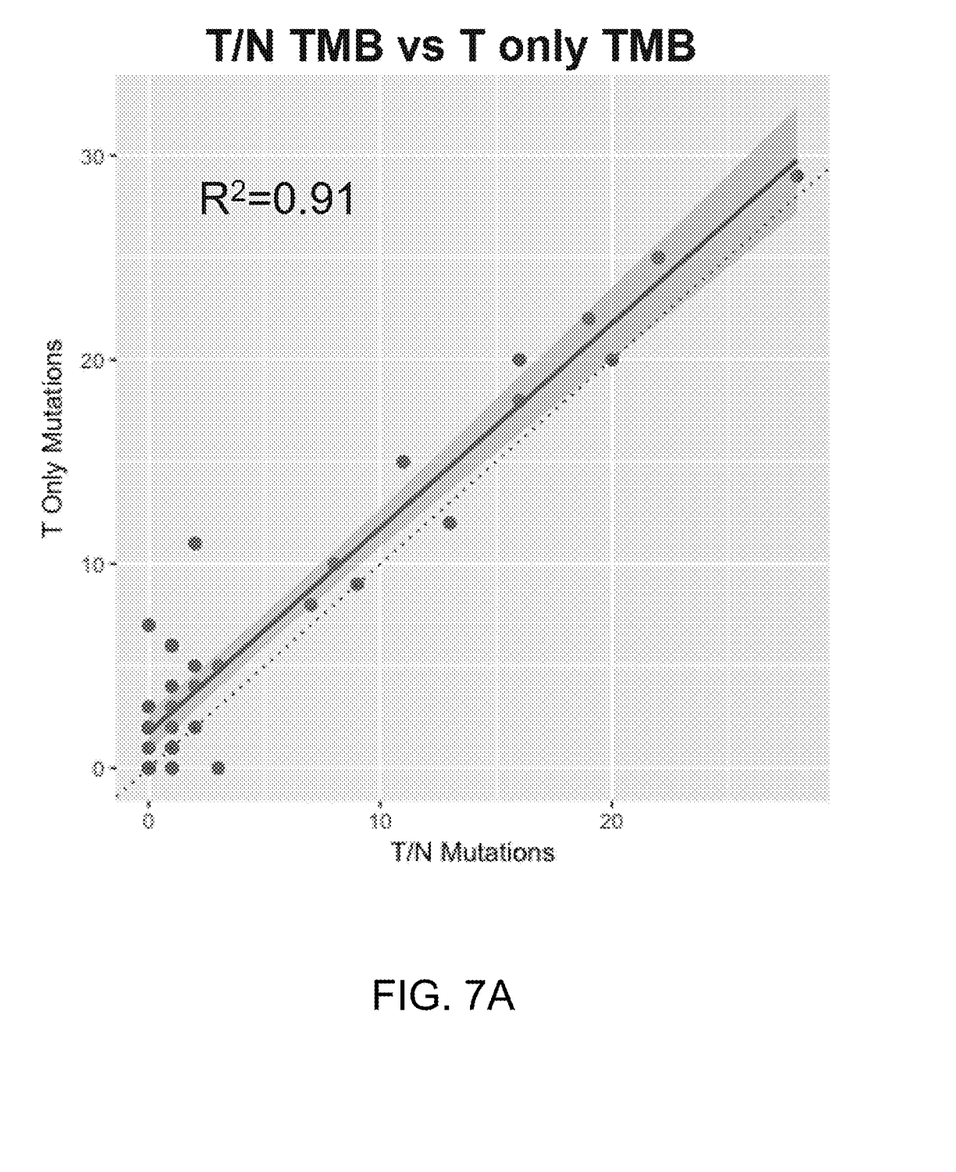
FIG. 7A depicts TMB in tumor only TMB (T only TMB) compared to whole blood cell TMB (T/N TMB).
Figure 7B:
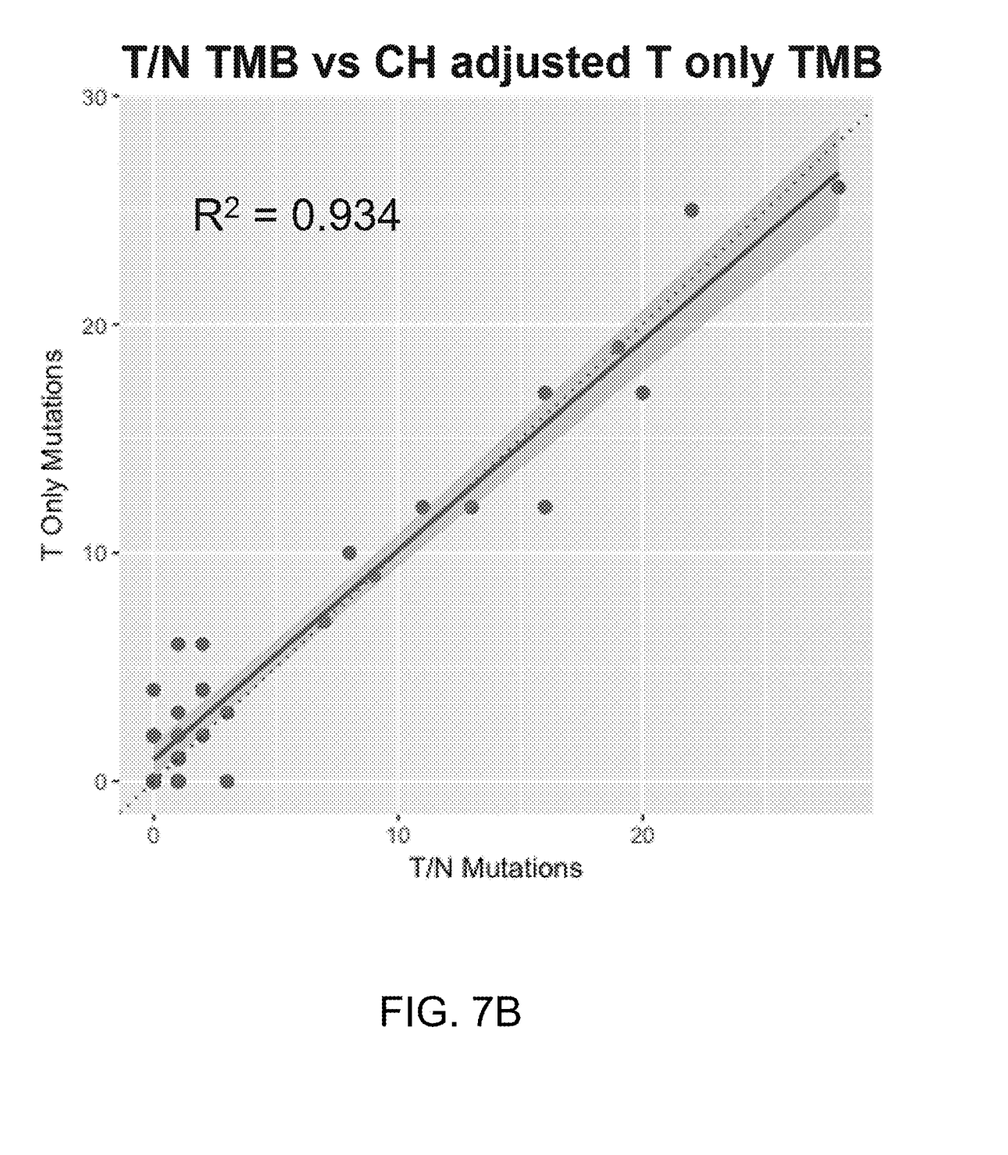
FIG. 7B depicts TMB in T/N TMB compared to clonal hematopoiesis adjusted T only TMB.

As shown in FIG. 7A, the TMB in tumor only TMB (T only TMB) compared to whole blood cell TMB (T/N TMB) correlated with an $R^2$ of 0.91 and tumor only TMB is higher than tumor normal TMB due to CH variants. As shown in FIG. 7B, the TMB in T/N TMB compared to clonal hematopoiesis adjusted T only TMB correlated to an $R^2$ of 0.934 and tumor only TMB is similar to tumor normal TMB.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of determining a tumor mutation burden of a tumor, comprising:
   (a) obtaining sequence data from a biological sample;
   (b) determining a plurality of variants from the sequence data;
   (c) excluding from the plurality of variants, variants having a catalogue of somatic mutations in cancer (COSMIC) count of greater than 50;
   (d) determining a number of cancer variants in the plurality of variants, wherein (d) comprises:
      (i) obtaining or having obtained the biological sample, the biological sample comprising a plurality of cell free DNA (cfDNA) fragments, wherein the plurality of cfDNA fragments comprise ctDNA;
      (ii) extracting the plurality of cfDNA fragments from the biological sample, wherein the plurality of cfDNA fragments comprise the plurality of variants;
      (iii) performing molecular profiling for each of the plurality of variants, comprising:
         (A) determining a variant allele frequency (VAF) for each of the plurality of variants, wherein the plurality of variants comprise cancer variants and hematopoietic cell variants, wherein the hematopoietic cell variants are associated with clonal hematopoiesis, and
         (B) generating a fragment size distribution profile to identify hematopoietic cell variants; and
      (iv) identifying cancer variants by removing the identified hematopoietic cell variants, the hematopoietic cell variants comprising mutations in TET2, TP53, DNMT3A, and/or CBL, and
   (e) calculating a tumor mutation burden value, wherein the tumor mutation burden value is a measurement of mutations carried by tumor cells that incorporates the number of cancer variants.

2. The method of claim 1, wherein calculating the tumor mutation burden value comprises dividing the number of cancer variants by effective panel size.

3. The method of claim 2, wherein the effective panel size comprises the total coding region with a coverage of greater than 500 times.

4. The method of claim 1, wherein the tumor mutation burden value is calculated as an average number of cancer variants per genomic region.

5. The method of claim 4, wherein the tumor mutation burden value is provided as a number of mutations per 50 kb.

6. The method of claim 4, wherein the tumor mutation burden value is provided as a number of mutations per 100 kb.

7. The method of claim 4, wherein the tumor mutation burden value is provided as a number of mutations per 1 Mb.

8. The method of claim 4, wherein the tumor mutation burden value is provided as a number of mutations per 10 Mb.

9. The method of claim 4, wherein the tumor mutation burden value is provided as a number of mutations per 100 Mb.

10. The method of claim 1, further comprising selecting a treatment for the tumor if the tumor mutation burden exceeds a TMB threshold.

11. The method of claim 10, further comprising administering the treatment.

12. The method of claim 1, further comprising removing germline variants from the plurality of variants.

13. The method of claim 12, wherein the germline variants are removed by applying a database filter or a proximity filter to the plurality of variants.

14. The method of claim 1, further comprising sequencing the cfDNA fragments to obtain sequence data.

15. The method of claim 14, further comprising aligning the sequence data with a reference sequence, and identifying variants in the sequence data.

16. The method of claim 1, wherein the ctDNA of the sample originates from a solid sample or a plasma sample.

17. The method of claim 16, wherein the solid sample is fixed.

18. The method of claim 16, wherein the sample comprises a tumor cell.

19. The method of claim 16, wherein the sample comprises a serum sample, a stool sample, a blood sample, or a tumor sample.

20. The method of claim 1, wherein at least steps (iii) and (iv) of the method is a computer-implemented method.

21. A method of treating a tumor, comprising:
    determining a tumor having a tumor mutation burden greater than or equal to 10 cancer variants according to the method of claim 1; and
    treating the tumor by administering an effective amount of a checkpoint inhibitor.

22. The method of claim 21, wherein the tumor is selected from the group consisting of a colorectal tumor, a lung tumor, an endometrium tumor, a uterine tumor, a gastric tumor, a melanoma, a breast tumor, a pancreatic tumor, a kidney tumor, a bladder tumor, and a brain tumor.

23. The method of claim 21, wherein the checkpoint inhibitor is selected from the group consisting of a CTLA-4 inhibitor, a PD-1 inhibitor, and a PD-L1 inhibitor.

24. The method of claim 21, wherein the checkpoint inhibitor is selected from the group consisting of Ipilimumab, Nivolumab, Pembrolizumab, Spartalizumab, Atezolizumab, Avelumab, and Durvalumab.

* * * * *